United States Patent
Cooper et al.

(10) Patent No.: US 9,453,812 B2
(45) Date of Patent: Sep. 27, 2016

(54) END-FILL ELECTROCHEMICAL-BASED ANALYTICAL TEST STRIP WITH PERPENDICULAR INTERSECTING SAMPLE-RECEIVING CHAMBERS

(71) Applicant: LifeScan Scotland Limited, Inverness (GB)

(72) Inventors: Alexander Cooper, Inverness (GB); Antony Smith, Dingwall (GB); Lynsey Whyte, Newtonmore (GB); Neil Whitehead, Dingwall (GB); David McColl, Inverness (GB); Brian Guthrie, Inverness (GB); Timothy Lloyd, Avoch (GB); Rossano Massari, Milan (IT); Christian Forlani, Milan (IT)

(73) Assignee: LifeScan Scotland Limited, Inverness (GB)

( * ) Notice: Subject to any disclaimer, the term of this patent is extended or adjusted under 35 U.S.C. 154(b) by 287 days.

(21) Appl. No.: 14/313,377

(22) Filed: Jun. 24, 2014

(65) Prior Publication Data

US 2015/0369769 A1 Dec. 24, 2015

(51) Int. Cl.
*G01N 17/00* (2006.01)
*G01N 27/327* (2006.01)
(Continued)

(52) U.S. Cl.
CPC ........ *G01N 27/327* (2013.01); *G01N 27/3272* (2013.01); *B01L 2300/0645* (2013.01); *G01N 31/164* (2013.01); *G01N 33/0031* (2013.01); *G01N 2030/645* (2013.01)

(58) Field of Classification Search
CPC ........... G01N 27/327; G01N 27/3272; G01N 31/164; G01N 2030/645; G01N 33/0031; B01L 2300/0645
See application file for complete search history.

(56) References Cited

U.S. PATENT DOCUMENTS

| 5,708,247 A | 1/1998 | McAleer et al. |
| 6,241,862 B1 | 6/2001 | McAleer et al. |

(Continued)

FOREIGN PATENT DOCUMENTS

| EP | 2292785 A1 | 3/2011 |
| GB | 2509140 A | 6/2014 |

(Continued)

OTHER PUBLICATIONS

Combined Search and Examination Report issued in Application No. GB 1223477.9, dated Apr. 9, 2013 (5 pages).

(Continued)

*Primary Examiner* — Dennis M White

(57) ABSTRACT

An electrochemical-based analytical test strip for the determination of an analyte (such as glucose) in a bodily fluid sample (for example, a whole blood sample) and/or a characteristic of the bodily fluid sample (e.g., hematocrit) includes a sample-entry chamber with a sample-application opening disposed on an end edge of the electrochemical-based analytical test strip, and first and second sample-determination chambers, each in direct fluidic communication with the sample-entry chamber. The electrochemical-based analytical test strip also includes first and second electrodes (such as first and second hematocrit electrodes) disposed in the first sample-determination chamber, and a third and fourth electrodes (for example working and reference electrodes) disposed in the second sample-determination chamber. Moreover, the first and second sample-determination chambers intersect the sample-entry chamber perpendicular (or nearly perpendicular) to one another and the first sample-determination chamber also intersects the sample-entry chamber in an aligned manner.

21 Claims, 8 Drawing Sheets

(51) Int. Cl.
*G01N 33/00* (2006.01)
*G01N 30/64* (2006.01)
*G01N 31/16* (2006.01)

(56) References Cited

U.S. PATENT DOCUMENTS

| | | |
|---|---|---|
| 6,284,125 B1 | 9/2001 | Hodges et al. |
| 6,733,655 B1 | 5/2004 | Davies et al. |
| 2005/0123443 A1 | 6/2005 | Fujiwara et al. |
| 2010/0096276 A1 | 4/2010 | Kojima et al. |
| 2010/0267161 A1 | 10/2010 | Wu et al. |
| 2012/0111739 A1 | 5/2012 | Pasqua et al. |

FOREIGN PATENT DOCUMENTS

| | | |
|---|---|---|
| GB | 2509325 A | 7/2014 |
| WO | 02/08763 A2 | 1/2002 |
| WO | 2008/044530 A1 | 4/2008 |
| WO | 2013/030375 A1 | 3/2013 |

OTHER PUBLICATIONS

International Search Report and Written Opinion issued in related International Patent Application No. PCT/EP2015/064151, dated Aug. 21, 2015, 15 pages.

END-FILL ELECTROCHEMICAL-BASED ANALYTICAL TEST STRIP WITH PERPENDICULAR INTERSECTING SAMPLE-RECEIVING CHAMBERS

BACKGROUND OF THE INVENTION

1. Field of the Invention

The present invention relates, in general, to medical devices and, in particular, to analytical test strips and related methods.

2. Description of Related Art

The determination (e.g., detection and/or concentration measurement) of an analyte in, or a characteristic of, a fluid sample is of particular interest in the medical field. For example, it can be desirable to determine glucose, ketone bodies, cholesterol, lipoproteins, triglycerides, acetaminophen, hematocrit and/or HbA1c concentrations in a sample of a bodily fluid such as urine, blood, plasma or interstitial fluid. Such determinations can be achieved using analytical test strips, based on, for example, visual, photometric or electrochemical techniques. Conventional electrochemical-based analytical test strips are described in, for example, U.S. Pat. Nos. 5,708,247, and 6,284,125, each of which is hereby incorporated in full by reference.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention, in which.

DETAILED DESCRIPTION OF ILLUSTRATIVE EMBODIMENTS

Figure 1:
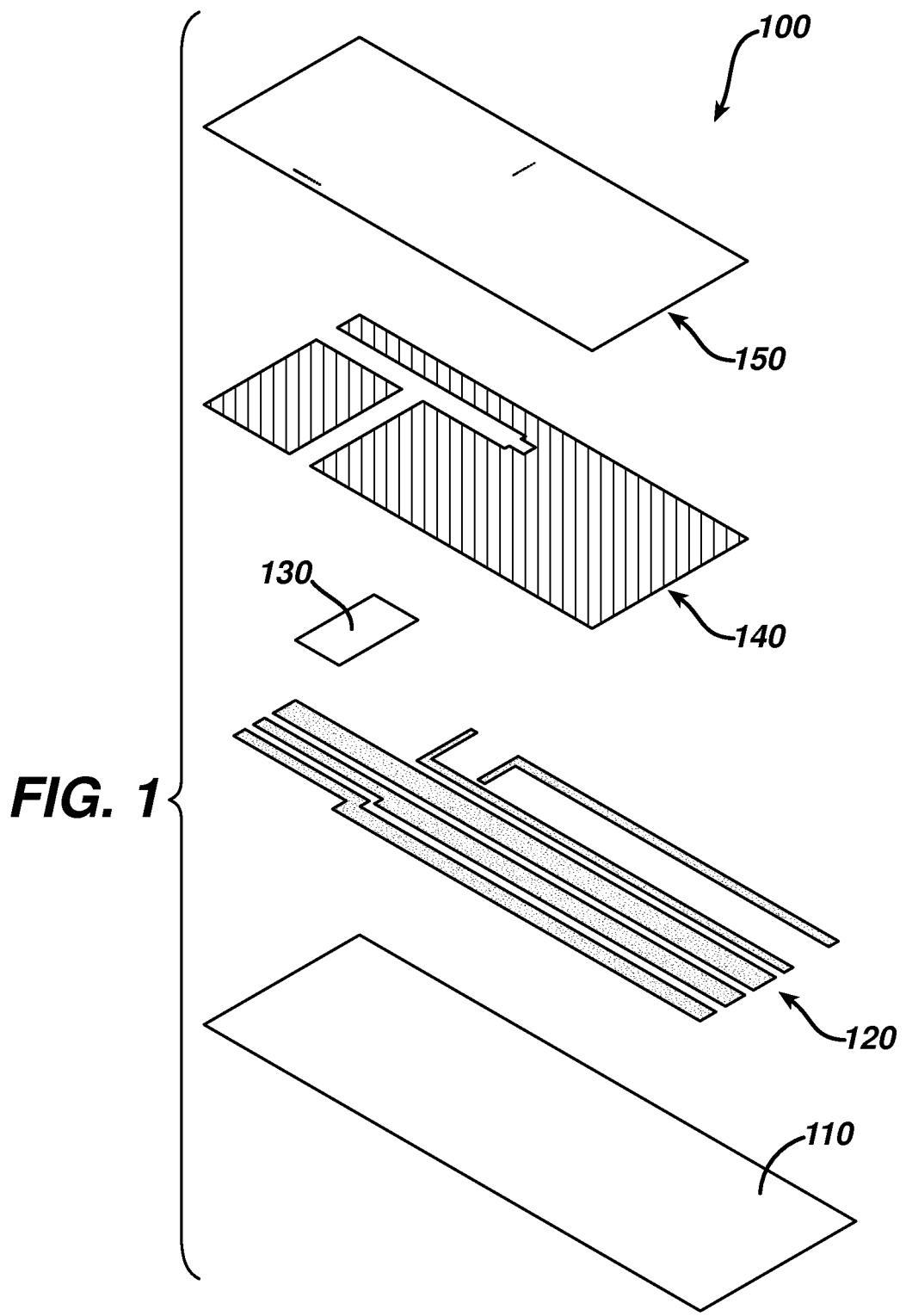
FIG. 1 is a simplified exploded view of an electrochemical-based analytical test strip according to an embodiment of the present invention.

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

As used herein, the terms "intersect" and "intersecting" refers to entities (such as a first sample-determination chamber and a second sample-determination chamber) approaching each other at, for example, a sample-entry chamber.

In general, an electrochemical-based analytical test strips for the determination of an analyte (such as glucose) in a bodily fluid sample (for example, a whole blood sample) and/or a characteristic of the bodily fluid sample (for example, hematocrit) according to embodiments of the present invention include a sample-entry chamber with a sample-application opening disposed on an end edge of the electrochemical-based analytical test strip, a first sample-determination chamber in direct fluidic communication with the sample-entry chamber, and a second sample-determination chamber in direct fluidic communication with the sample-entry chamber.

The electrochemical-based analytical test strips also include a first electrode and a second electrode disposed in the first sample-determination chamber and at least a third electrode and a fourth electrode disposed in the second sample-determination chamber. Furthermore, the first sample-determination chamber and the second sample-determination chamber intersect the sample-entry chamber perpendicular (or nearly perpendicular) to one another, and the first sample-determination chamber intersects the sample-entry chamber in an aligned manner (i.e., aligned with respect to the direction of bodily fluid flow from the sample-application opening, through the sample-entry-chamber and into the first sample-determination chamber).

Electrochemical-based analytical test strips according to embodiments of the present invention are beneficial in that, for example, the first sample-determination chamber and second sample-determination chamber fill in an acceptable manner (for example, filled with 100% coverage of any electrodes therein) during use. In addition, the bodily fluid sample that encounters the first electrode and the second electrode in the first sample-determination chamber has not passed through the second sample-determination chamber. This enables the use of a reagent layer in the second sample-determination chamber without any cross-contamination of that reagent layer into the first sample-determination chamber. Furthermore, the disposition of the sample-application opening on an end edge (i.e. distal edge) of the electrochemical-based analytical test strip provides a user with an intuitive sample application procedure with easy electrochemical-based test strip handling. Moreover, electrochemical-based analytical test strips according to embodiments of the present invention can be manufactured using relatively inexpensive and simple conventional processes and materials.

Figure 2:
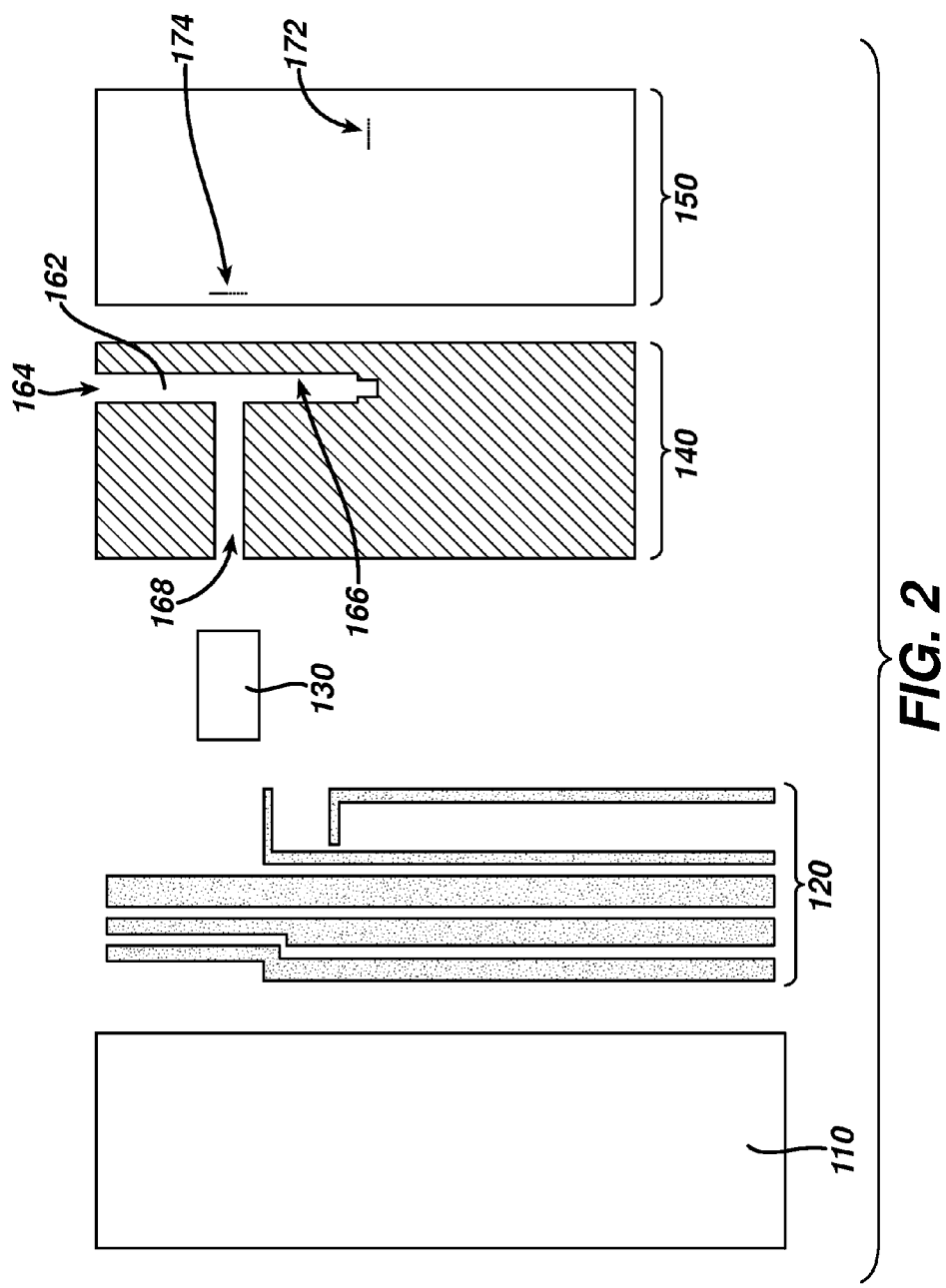
FIG. 2 is a sequence of simplified top views of the various layers of the electrochemical-based analytical test strip of FIG. 1.
Figure 3:
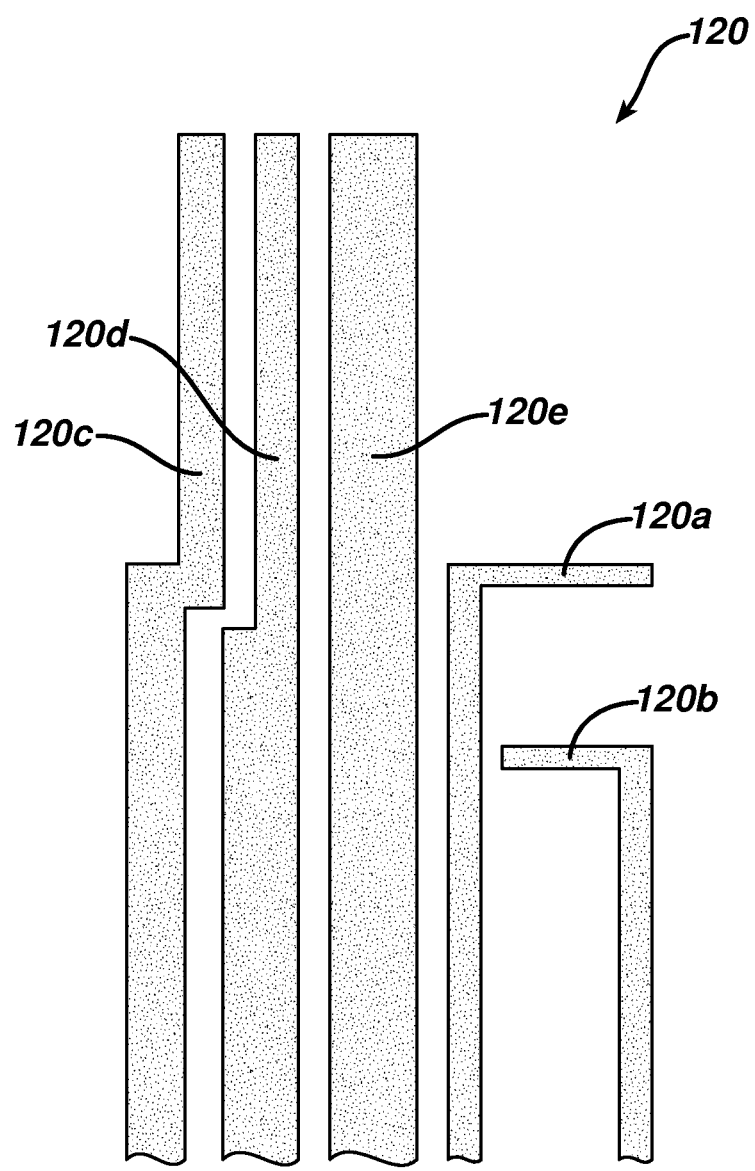
FIG. 3 is a simplified top view representation of a portion of a patterned conductor layer of the electrochemical-based analytical test strip of FIG. 1.
Figure 4:
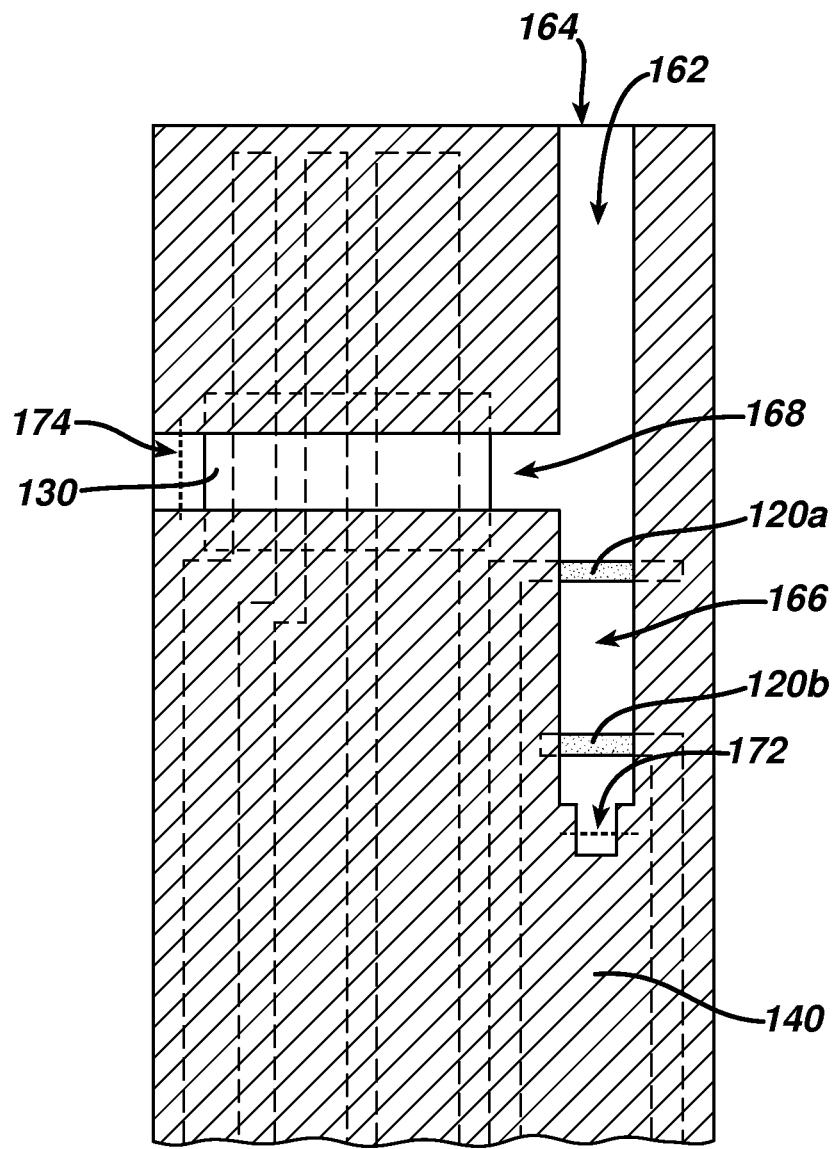
FIG. 4 is a simplified top view of the portion of the patterned conductor layer, a portion of a spacer layer and an enzymatic reagent layer of the electrochemical-based analytical test strip of FIG. 1 with the reagent layer depicted as transparent to highlight the patterned conductor layer thereunder.

FIG. 1 is a simplified exploded view of an electrochemical-based analytical test strip 100 according to an embodiment of the present invention. FIG. 2 is a sequence of simplified top views of various layers of electrochemical-based analytical test strip 100. FIG. 3 is a simplified top view representation of a portion of a patterned conductor layer of the electrochemical-based analytical test strip 100. FIG. 4 is a simplified top view of the portion of the patterned conductor layer, a portion of a spacer layer and an enzymatic reagent layer of electrochemical-based analytical test strip 100 with the reagent layer depicted as transparent to highlight the patterned conductor layer thereunder.

Referring to FIGS. 1-4, electrochemical-based analytical test strip 100 for the determination of an analyte (such as glucose) in a bodily fluid sample (for example, a whole blood sample) and for the determination of hematocrit in the bodily fluid sample includes an electrically-insulating substrate layer 110, a patterned conductor layer 120, a reagent layer 130, a patterned spacer layer 140, and a hydrophilic top layer 150.

The disposition and alignment of electrically-insulating substrate layer 110, patterned conductor layer 120 (which includes a first electrode 120a, second electrode 120b, third electrode 120c, fourth electrode 120d and fifth electrode 120e; see FIGS. 3 and 4 in particular), patterned spacer layer 140, and hydrophilic top layer 150 of electrochemical-based analytical test strip 100 are such that a sample-entry chamber 162 (with sample-application opening 164), first sample-determination chamber 166 and second sample-determination chamber 168 are defined within electrochemical-based analytical test strip 100. Moreover, sample-application opening 164 is disposed on an end edge (also known as a distal end edge or simply distal end) of electrochemical-based analytical test strip 100. Since electrochemical-based analytical test strip 100 is elongated in shape, the term "end" refers to a minor edge (i.e., a relatively short edge such as a distal end edge) as opposed to a major lateral edge (i.e., a relatively long side edge that can also be described simply as lateral side).

First and second sample-determination chambers 166 and 168 can have any suitable dimensions including, for example, a height of 0.13 mm.

In electrochemical-based analytical test strip 100, first electrode 120a and second electrode 120b are configured for the determination of the characteristic (for example, the hematocrit) of a bodily fluid sample introduced into first sample-determination chamber 166 via sample-entry chamber 162. First electrode 120a and second electrode 120b are, therefore, also referred to as hematocrit electrodes.

In addition, third electrode 120c and fourth electrode 120d are configured as working electrodes and fifth electrode 120e is configured as a counter-reference electrode. Although, for the purpose of explanation only, electrochemical-based analytical test strip 100 is depicted as including a total of five electrodes, embodiments of electrochemical-based analytical test strips, including embodiments of the present invention, can include any suitable number of electrodes. First and second electrodes 120a and 120b, respectively, can have areas of, for example, 0.14 square-mm (e.g., a 0.2 mm height and a 0.7 mm width with the width defined by patterned spacer layer 140). Working electrodes 120c and 120d can each have, for example, an area of 0.28 square-mm and counter/reference electrode 120e can have, for example, an area of 0.56 square-mm.

Patterned conductor layer 120, including electrodes 120a, 120b, 120c, 120d and 120e, of electrochemical-based analytical test strip 100 can be formed of any suitable conductive material including, for example, gold, palladium, platinum, indium, titanium-palladium alloys and electrically conducting carbon-based materials including carbon inks. Referring in particular to FIG. 4, the disposition of third electrode 120c, fourth electrode 120d and fifth electrode 120e and reagent layer 130 are such that electrochemical-based analytical test strip 100 is configured for the electrochemical determination of an analyte (glucose) in a bodily fluid sample (whole blood) that has filled second sample-determination chamber 168.

Moreover, first electrode 120a and second electrode 120b are disposed in first sample-determination chamber 166 such that electrochemical-based analytical test strip 100 is configured for the determination of hematocrit in a whole blood sample that has filled first sample-determination chamber 166. During use, a bodily fluid sample is applied to electrochemical-based analytical test strip 100 and transferred to both first sample-determination chamber 166 (thereby operatively contacting the first and second electrodes 120a and 120b) and to the second sample-determination chamber 168, thereby operatively contacting electrodes 120c, 120d and 120e. The determination of hematocrit using electrodes of an analytical test strip is described in, for example, U.S. patent application Ser. Nos. 61/581,100; 61/581,097; 61/581,089; 61/530,795 and 61/530,808, each of which is hereby incorporated in full by reference.

Since in electrochemical-based analytical test strip 100 first sample-determination chamber 166 is reagent-less (i.e., enzymatic reagent layer 130 is not disposed within first sample-determination chamber 166, which is therefore devoid of reagent) and sample flows directly from sample-entry chamber 162 into first sample-determination chamber 166 (as well as directly into second sample-determination chamber 168), there is no risk bodily fluid sample flow introducing an unwanted reagent into the first sample-determination chamber from the second sample-determination chamber.

Electrically-insulating substrate layer 110 can be any suitable electrically-insulating substrate layer known to one skilled in the art including, for example, a nylon substrate, polycarbonate substrate, a polyimide substrate, a polyvinyl chloride substrate, a polyethylene substrate, a polypropylene substrate, a glycolated polyester (PETG) substrate, or a polyester substrate. The electrically-insulating substrate layer can have any suitable dimensions including, for example, a width dimension of about 5 mm, a length dimension of about 27 mm and a thickness dimension of about 0.5 mm.

Electrically-insulating substrate layer 110 provides structure to electrochemical-based analytical test strip 100 for ease of handling and also serves as a base for the application (e.g., printing or deposition) of subsequent layers (e.g., a patterned conductor layer). It should be noted that patterned conductor layers employed in analytical test strips according to embodiments of the present invention can take any suitable shape and be formed of any suitable materials including, for example, metal materials and conductive carbon materials.

Patterned spacer layer 140 can be formed, for example, from a screen-printable pressure sensitive adhesive commercially available from Apollo Adhesives, Tamworth, Staffordshire, UK. In the embodiment of FIGS. 1 through 5, patterned spacer layer 140 defines outer walls of the sample-entry chamber 162, first sample-determination chamber 166 and the second sample-determination chamber 168. Patterned spacer layer 140 can have a thickness of, for example, approximately 75 microns, be electrically nonconductive, and be formed of a polyester material with top and bottom side acrylic-based pressure sensitive adhesive.

Hydrophilic top layer 150 can be, for example, a clear film with hydrophilic properties that promote wetting and filling of electrochemical-based analytical test strip 100 by a fluid sample (e.g., a whole blood sample). Such clear films are commercially available from, for example, 3M of Minneapolis, Minn. U.S.A. and Coveme (San Lazzaro di Savena, Italy). Hydrophilic top layer 150 can be, for example, a polyester film coated with a surfactant that provides a hydrophilic contact angle <10 degrees. Hydrophilic top layer 150 can also be a polypropylene film coated with a surfactant or other surface treatment, e.g., a MESA coating. Hydrophilic top layer 150 can have a thickness, for example, of approximately 100 µm. Moreover, in the embodiment of FIGS. 1-5, hydrophilic top layer 150 is patterned to provide air vents 172 for first sample-determination chamber 166 (as depicted in FIGS. 2 and 4) and air vents 174 for second sample-determination chamber 168 (as also depicted in FIGS. 2 and 4).

Reagent layer 130 can include any suitable enzymatic reagents, with the selection of enzymatic reagents being dependent on the analyte to be determined. For example, if glucose is to be determined in a blood sample, reagent layer 130 can include a glucose oxidase or glucose dehydrogenase along with other components necessary for functional operation. Reagent layer 130 can include, for example, glucose oxidase, tri-sodium citrate, citric acid, polyvinyl alcohol, hydroxyl ethyl cellulose, potassium ferrocyanide, antifoam, cabosil, PVPVA, and water. Further details regarding reagent layers, and electrochemical-based analytical test strips in general, are in U.S. Pat. Nos. 6,241,862 and 6,733,655, the contents of which are hereby fully incorporated by reference.

Electrochemical-based analytical test strip 100 can be manufactured, for example, by the sequential aligned formation of patterned conductor layer 120, reagent layer 130, patterned spacer layer 140, and hydrophilic top layer 150 and onto electrically-insulating substrate layer 110. Any suitable techniques known to one skilled in the art can be used to accomplish such sequential aligned formation, including, for example, screen printing, photolithography, photogravure, chemical vapour deposition and tape lamination techniques.

Figure 5:
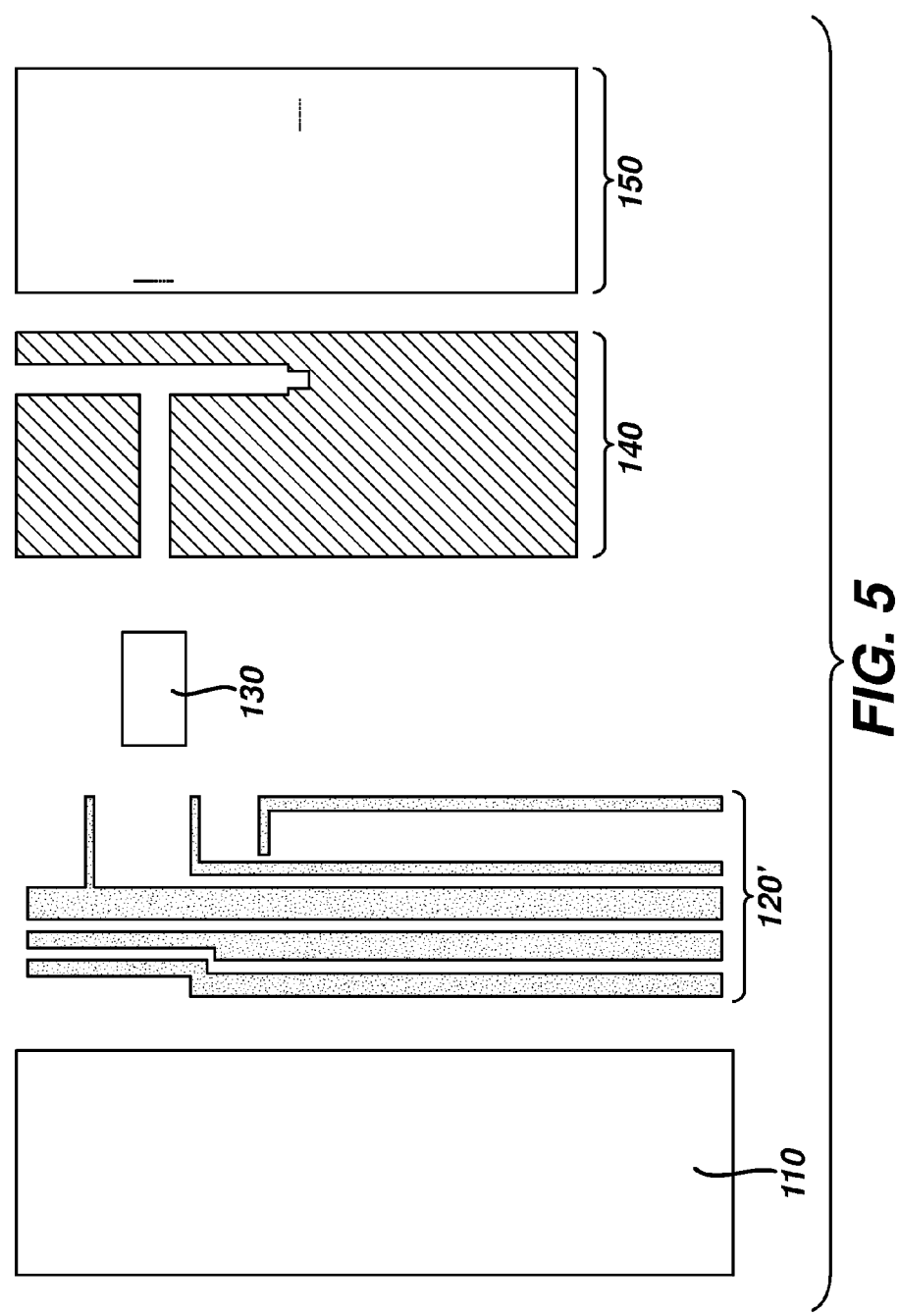
FIG. 5 is a sequence of simplified top views of the various layers of another electrochemical-based analytical test strip according to the present invention.
Figure 6:
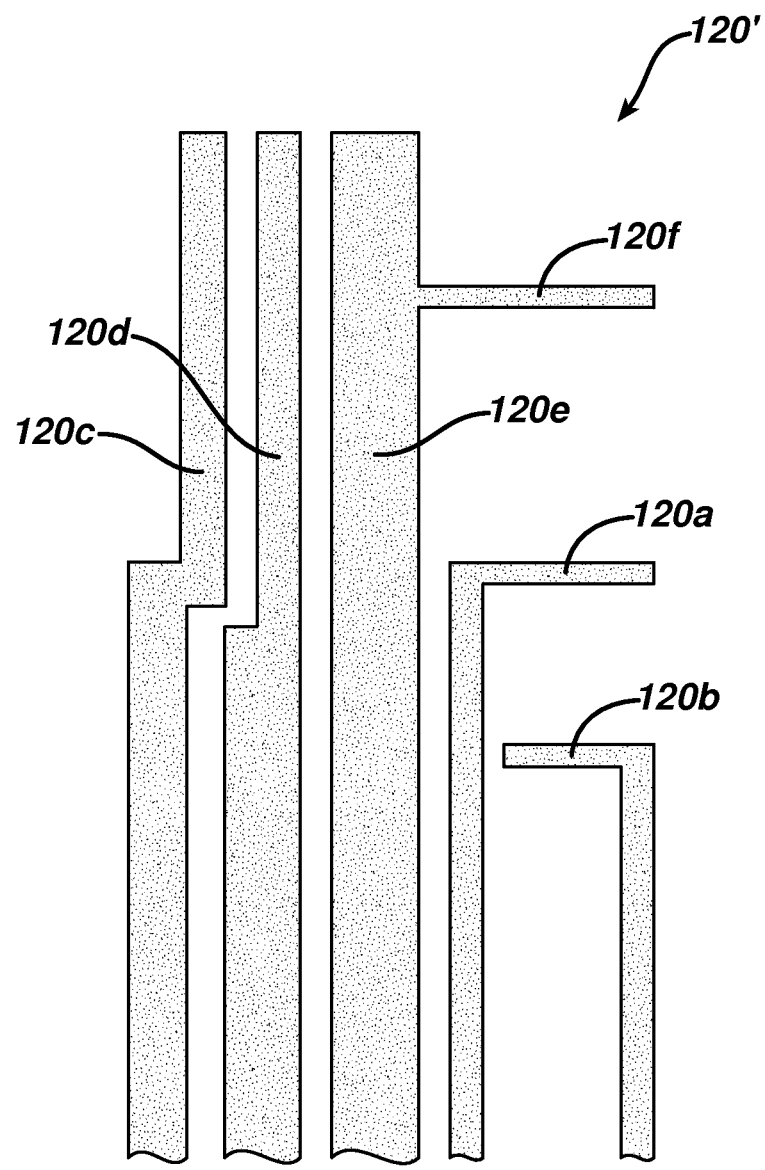
FIG. 6 is a simplified top view representation of a portion of a patterned conductor layer of the electrochemical-based analytical test strip of FIG. 5.
Figure 7:
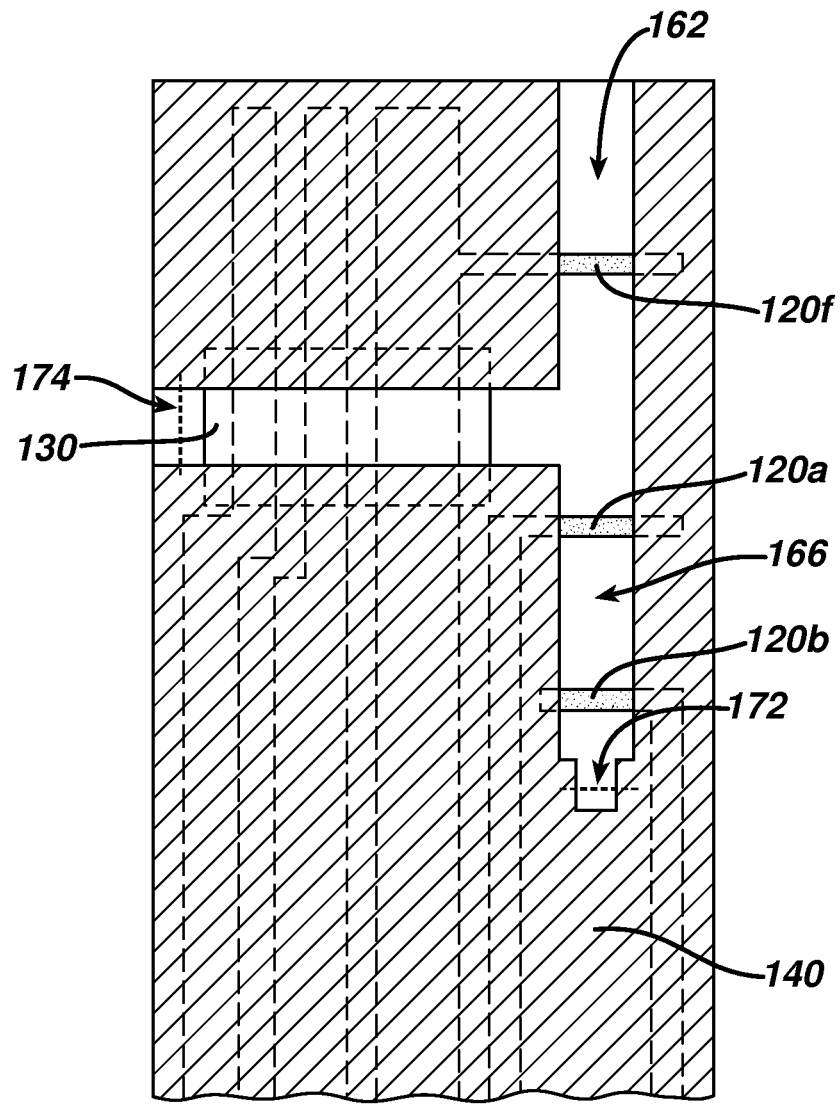
FIG. 7 is a simplified top view of the portion of the patterned conductor layer, a portion of a spacer layer and an enzymatic reagent layer of the electrochemical-based analytical test strip of FIG. 5, with the reagent layer depicted as transparent to highlight the patterned conductor layer thereunder.

FIG. 5 is a sequence of simplified top views of the various layers of another electrochemical-based analytical test strip 200 according to the present invention. FIG. 6 is a simplified top view representation of a portion of a patterned conductor layer of electrochemical-based analytical test strip 200. FIG. 7 is a simplified top view of the portion of the patterned conductor layer, a portion of a spacer layer and an enzymatic reagent layer of electrochemical-based analytical test strip 200, with the reagent layer depicted as transparent to highlight the patterned conductor layer thereunder. In FIGS. 5, 6, and 7, like numerals indicate like elements in electrochemical-based analytical test strip 100. However, in electrochemical-based analytical test strip 200, the patterned conductor layer is labeled 120' to distinguish it from patterned conductor layer 120 of electrochemical-based analytical test strip 100.

Electrochemical-based analytical test strip 200 is essentially identical to electrochemical test strip 100 but with the addition of an additional electrode 120f of patterned conductor layer 120' disposed in sample-entry chamber 162. Additional electrode 120f is configured as a "shield" electrode that reduces a deleterious electrical proximity effect caused by a user's body becoming a part of the electrical circuit(s) within the electrochemical-based analytical test strip. Such an electrical proximity effect can interfere with proper operation of the electrochemical-based analytical test strip by, for example, interfering with phase-angle measurements between the first electrode and second electrode disposed in the first sample-determination chamber. A reduction in the proximity effect can be achieved, for example, by configuring the shield electrode to provide a more favored ground path for the electrochemical-based analytical test strip than a ground path provided by a user's body (such as a user's finger).

In the embodiment of electrochemical-based analytical test strip 200, shield electrode 120f is in electrical communication with fifth electrode 120e, which is configured as a counter/reference electrode. Shield electrode 120f can have an area, for example, of 0.14 square-mm.

Figure 8:
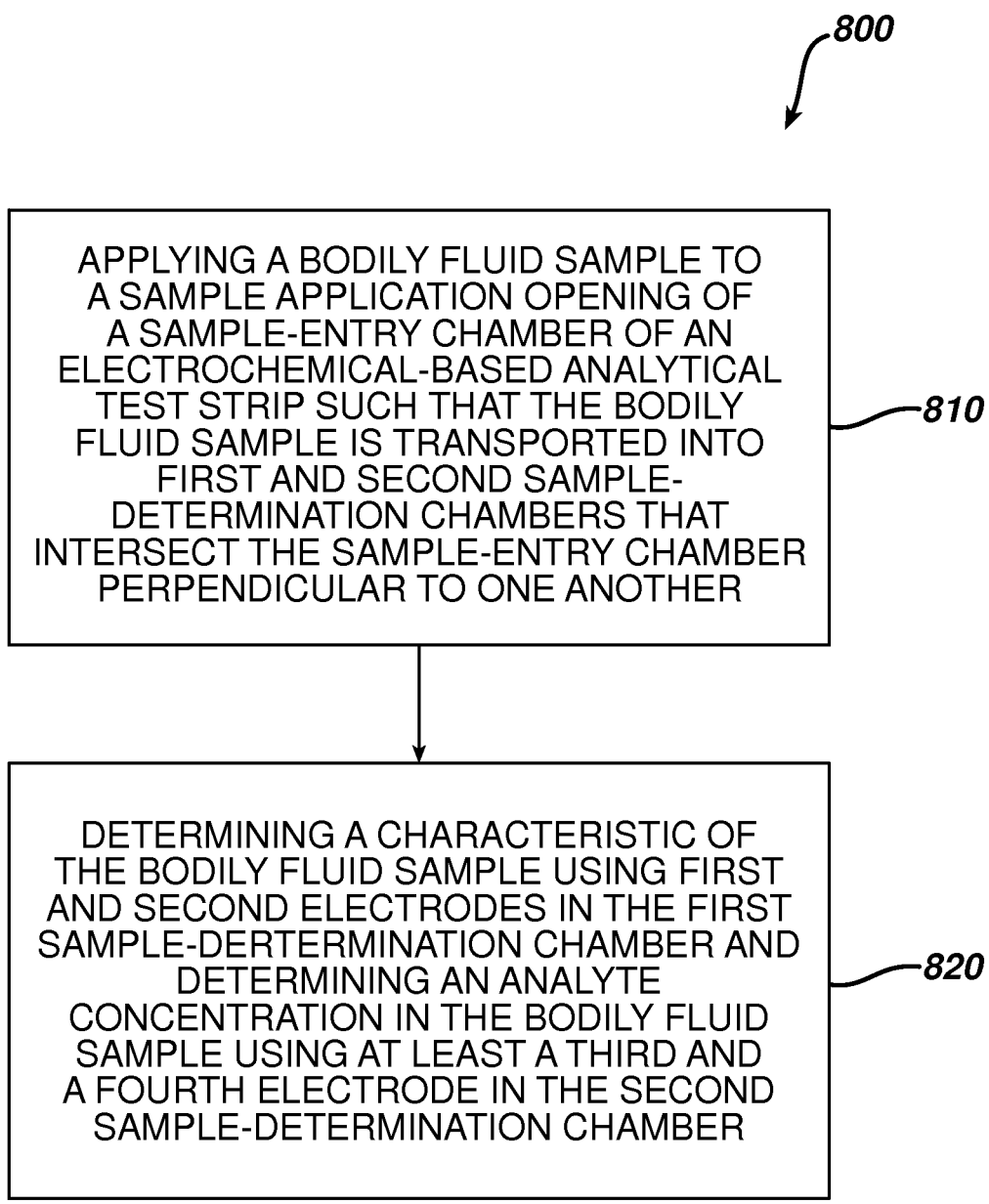
FIG. 8 is a flow diagram depicting stages in a method for determining an analyte in a bodily fluid sample according to an embodiment of the present invention.

FIG. 8 is a flow diagram depicting stages in a method 800 for determining an analyte (such as glucose) in a bodily fluid sample (for example, a whole blood sample) and/or a characteristic of the bodily fluid sample (e.g., hematocrit) according to an embodiment of the present invention. Method 800 includes (see step 810 of FIG. 8) applying a bodily fluid sample to a sample application opening of a sample-entry chamber of an electrochemical-based analytical test strip such that the applied bodily fluid sample is transported into a first sample-determination chamber and a second sample-determination chamber of the electrochemical-based analytical test strip.

At step 820 of FIG. 8, a characteristic of the applied bodily fluid sample is determined, using a first electrode and a second electrode disposed in the first sample-determination chamber, and an analyte in the bodily fluid sample using at least a third electrode and a fourth electrode disposed in the second sample-determination chamber.

In method 800, the first sample-determination chamber and the second sample-determination chamber intersect the single sample-entry chamber perpendicular (or nearly perpendicular) to one another, and the first sample-determination chamber intersects the sample-entry chamber in an aligned manner. Moreover, the sample-application opening is disposed on an end edge surface of the electrochemical-based analytical test strip.

Once apprised of the present disclosure, one skilled in the art will recognize that method 800 can be readily modified to incorporate any of the techniques, benefits, features and characteristics of electrochemical-based analytical test strips according to embodiments of the present invention and described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. An electrochemical-based analytical test strip for the determination of an analyte in a bodily fluid sample, the electrochemical-based analytical test strip comprising:

a sample-entry chamber with a sample-application opening, the sample-application opening disposed on an end edge of the electrochemical-based analytical test strip;

a first sample-determination chamber in direct fluidic communication with the sample-entry chamber;

a second sample-determination chamber in direct fluidic communication with the sample-entry chamber;

a first electrode and a second electrode disposed in the first sample-determination chamber;

at least a third electrode and a fourth electrode disposed in the second sample-determination chamber, and wherein the first sample-determination chamber and the second sample-determination chamber intersect the sample-entry chamber nearly perpendicular to one another; and wherein the first sample-determination chamber intersects the sample-entry chamber in an aligned manner.

2. The electrochemical-based analytical test strip of claim 1 further including:

a reagent layer disposed on the at least third electrode and fourth electrode.

3. The electrochemical-based analytical test strip of claim 1 further including a shield electrode, the shield electrode being disposed in the sample-entry chamber between the sample-application opening and the first sample-determination chamber.

4. The electrochemical-based analytical test strip of claim 3 wherein the shield electrode is configured to reduce an electrical proximity effect of a user's body applying a bodily fluid sample to the electrochemical-based analytical test strip.

5. The electrochemical-based analytical test strip of claim 1, further comprising:

an electrically insulating substrate layer;

a patterned conductor layer disposed over the electrically-insulating substrate layer, the patterned conductive layer including the first electrode, second electrode and at least third electrode and fourth electrode;

a reagent layer disposed over the at least third electrode and fourth electrode of the patterned conductor layer;

a patterned spacer layer; and a hydrophilic top layer, wherein the electrically insulating substrate layer, patterned spacer layer, the hydrophilic layer and the hydrophilic top layer essentially define the sample-entry chamber, first sample-determination chamber and second sample-determination chamber.

6. The electrochemical-based analytical test strip of claim 5 wherein the first sample-determination chamber is a reagent-less sample-determination chamber.

7. The electrochemical-based analytical test strip of claim 1 wherein the first electrode and second electrode are configured for the determination of hematocrit of a bodily fluid sample in the first sample-determination chamber.

8. The electrochemical-based analytical test strip of claim 1 wherein the at least third electrode and fourth includes a first working electrode, a second working electrode and a counter/reference electrode.

9. The electrochemical-based analytical test strip of claim 8 further including shield electrode disposed in the sample-entry chamber between the sample-application opening and the first sample-determination chamber, the shield electrode being in electrical communication with the counter/reference electrode.

10. The electrochemical-based analytical test strip of claim 1 wherein the first and second electrodes are separated by a distance in the range of 0.9 mm to 1.5 mm in the first sample-receiving chamber.

11. The electrochemical-based analytical test strip of claim 10 wherein the analyte is glucose and the bodily fluid sample is blood.

12. A method for determining an analyte in a bodily fluid sample, the method comprising:

applying a bodily fluid sample to a sample application opening of a sample-entry chamber of an electrochemical-based analytical test strip such that the applied bodily fluid sample is transported into a first sample-determination chamber and a second sample-determination chamber of the electrochemical-based analytical test strip, and determining a characteristic of the applied bodily fluid sample, using a first electrode and a second electrode disposed in the first sample-determination chamber, and an analyte in the bodily fluid sample using at least a third electrode and a fourth electrode disposed in the second sample-determination chamber;

wherein the first sample-determination chamber and the second sample-determination chamber intersect the single sample-entry chamber nearly perpendicular to one another; and wherein the first sample-determination chamber intersects the sample-entry chamber in an aligned manner, and wherein the sample-application opening is disposed on an end edge surface of the electrochemical-based analytical test strip.

13. The method of claim 12 wherein the bodily fluid sample is whole blood.

14. The method of claim 13 wherein the analyte is glucose.

15. The method of claim 13 wherein the characteristic is hematocrit.

16. The method of claim 13 wherein the electrochemical-based analytical test strip includes a shield electrode disposed in the sample-entry chamber.

17. The method of claim 16 wherein the shield electrode is configured to reduce an electrical proximity effect of a user's body applying a bodily fluid sample to the electrochemical-based analytical test strip.

18. The method of claim 17 wherein the shield electrode is in electrical communication with one of the at least third electrode and fourth electrode.

19. The method of claim 13 wherein the electrochemical-based analytical test strip includes a reagent layer disposed in the second sample-determination chamber.

20. The method of claim 13 wherein the first sample-determination chamber is devoid of reagent.

21. The method of claim 13 wherein the first and second electrodes are separated by a distance in the range of 0.9 mm to 1.5 mm in the first sample-receiving chamber.

* * * * *